United States Patent
McDonell et al.

(10) Patent No.: US 10,070,988 B2
(45) Date of Patent: Sep. 11, 2018

(54) DEVICES, SYSTEMS, AND METHODS FOR VISUALIZATION OF MOVING TISSUE WITH STROBED ILLUMINATION

(71) Applicant: Novartis AG, Basel (CH)

(72) Inventors: Brian William McDonell, Irvine, CA (US); Tammo Heeren, Aliso Viejo, CA (US)

(73) Assignee: Novartis AG, Basel (CH)

( * ) Notice: Subject to any disclaimer, the term of this patent is extended or adjusted under 35 U.S.C. 154(b) by 798 days.

(21) Appl. No.: 14/574,630

(22) Filed: Dec. 18, 2014

(65) Prior Publication Data

US 2016/0175149 A1  Jun. 23, 2016

(51) Int. Cl.
  *A61F 9/007* (2006.01)
  *A61B 90/30* (2016.01)

(52) U.S. Cl.
  CPC .... *A61F 9/00745* (2013.01); *A61B 2090/306* (2016.02); *A61F 9/00736* (2013.01)

(58) Field of Classification Search
  CPC .......................................... A61F 9/007–9/0079
  See application file for complete search history.

(56) References Cited

U.S. PATENT DOCUMENTS

| | | | |
|---|---|---|---|
| 3,026,449 A | 3/1962 | Rappaport | |
| 3,826,557 A | 7/1974 | Lobb et al. | |
| 4,652,093 A * | 3/1987 | Stephen | A61B 1/227 356/23 |
| 4,788,866 A | 12/1988 | Tanimoto et al. | |
| 5,597,381 A * | 1/1997 | Rizzo, III | A61F 2/14 128/898 |
| 6,778,764 B2 | 8/2004 | Barghini et al. | |
| 8,747,426 B2 * | 6/2014 | Underwood | A61F 9/00763 606/171 |
| 2007/0156129 A1 * | 7/2007 | Kovalcheck | A61B 18/14 606/39 |
| 2011/0118729 A1 * | 5/2011 | Heeren | A61B 18/1477 606/41 |
| 2011/0144641 A1 * | 6/2011 | Dimalanta, Jr. | A61B 18/1477 606/45 |

(Continued)

FOREIGN PATENT DOCUMENTS

| | | |
|---|---|---|
| EP | 501008 B1 | 5/1997 |
| WO | 2016100044 A1 | 6/2016 |

*Primary Examiner* — Zade Coley (57) ABSTRACT

Devices, systems, and methods for visualizing moving tissue with strobed light are provided. A surgical system includes a surgical device configured to operate on anatomy at a first frequency such that the anatomy moves at the first frequency when the surgical device is in contact therewith; and a light source configured to provide pulses of light at a second frequency to illuminate the moving anatomy; wherein the second frequency is different than the first frequency. A method of treating an ophthalmic condition includes operating a surgical device at a first frequency such that anatomy moves at the first frequency when the surgical device is contacted therewith; and controlling a light source to provide pulses of light at a second frequency to illuminate the moving anatomy; wherein the second frequency is different than the first frequency. An ophthalmic surgical system includes a cutting probe, a strobed light source, and a computing device.

10 Claims, 6 Drawing Sheets

(56) References Cited

U.S. PATENT DOCUMENTS

2011/0230728 A1* 9/2011 Artsyukhovich ...... A61B 90/20
 600/249
2013/0041355 A1* 2/2013 Heeren .................. A61B 18/14
 606/5
2013/0150875 A1* 6/2013 McDonell ........... A61F 9/00763
 606/170
2015/0173948 A1* 6/2015 Heeren ............... A61F 9/00736
 606/171

* cited by examiner

DEVICES, SYSTEMS, AND METHODS FOR VISUALIZATION OF MOVING TISSUE WITH STROBED ILLUMINATION

BACKGROUND

The present invention pertains to ophthalmic surgical devices, systems, and methods. More particularly, but not by way of limitation, the present invention pertains to devices, systems, and methods for illuminating tissue in the eye that has periodic movement resulting from the periodic movement of a surgical probe in contact therewith.

Microsurgical procedures frequently require precision cutting and/or removing various body tissues. For example, certain ophthalmic surgical procedures require cutting and removing portions of the vitreous humor, a transparent jelly-like material that fills the posterior segment of the eye. The vitreous humor, or vitreous, is composed of numerous microscopic fibrils that are often attached to the retina. Therefore, cutting and removing the vitreous must be done with great care to avoid traction on the retina, the separation of the retina from the choroid, a retinal tear, or, in the worst case, cutting and removal of the retina itself. In particular, delicate operations such as mobile tissue management (e.g., cutting and removal of vitreous near a detached portion of the retina or a retinal tear), vitreous base dissection, and cutting and removal of membranes are particularly difficult.

Microsurgical cutting probes, such as vitrectomy probes, conventionally operate with high cutting frequencies. A pneumatic system can drive the cutting portion of the microsurgical cutting probe. The pneumatic system has a pulsatile nature, which causes the cutting portion of the microsurgical cutting probe to move in a pulsatile manner. When the microsurgical cutting probe is contacted with tissue in the eye, the tissue can acquire a synchronous, pulsatile movement. To a surgeon viewing the procedure through a surgical microscope, the tissue appears blurry as it moves at a frequency equal to that of the microsurgical cutting probe. The actual amplitude and shape of the moving tissue are obscured at such high frequencies. Thus, it is difficult for the surgeon to exercise the great care necessary to evaluate the tissue is being cut.

The present disclosure is directed to addressing one or more of the deficiencies in the prior art.

SUMMARY

The presented solution fills an unmet medical need with a unique solution to illuminate tissue in the eye with a strobed light source during a surgical procedure. The strobed light source and the surgical probe are operated at different frequencies. The tissue being operated on appears to move with a frequency that is slow enough to be evaluated by a surgeon.

In one exemplary aspect, the present disclosure is directed to a surgical system. The system includes a surgical device configured to operate on anatomy at a first frequency such that the anatomy moves at the first frequency when the surgical device is contact therewith; and a light source configured to provide pulses of light at a second frequency to illuminate the moving anatomy; wherein the second frequency is different than the first frequency.

In one aspect, the surgical device is an ophthalmic surgical device, and wherein the anatomy is a portion of an eye. In one aspect, the ophthalmic surgical device is at least one of a vitrectomy probe, a phacoemulsification probe, and vibrating shears. In one aspect, the light source is configured to selectively provide continuous light and the pulses of light. In one aspect, the light source is configured to generate the pulses of light at the second frequency only when the first frequency is greater than a threshold frequency. In one aspect, the threshold frequency is adjustable. In one aspect, the system further includes a computing device communicatively coupled to the surgical device and the light source, wherein the computing device is configured to provide a first control signal to the surgical device such that the surgical device operates at the first frequency and to provide a second control signal to the light source such that the light source generates the pulses of light at the second frequency. In one aspect, the computing device is configured to generate at least one of the first control signal and the second control signal in response to a user input. In one aspect, the system further includes an interface device communicatively coupled to the computing device, wherein the interface device is configured to receive the user input corresponding to at least one of the first frequency, the second frequency, a threshold frequency, a frequency offset, and a relationship between the first frequency and the second frequency.

In an additional exemplary aspect, the present disclosure is directed to a method of treating an ophthalmic condition. The method includes operating a surgical device at a first frequency such that anatomy moves at the first frequency when the surgical device is contacted therewith; and controlling a light source to provide pulses of light at a second frequency to illuminate the moving anatomy; wherein the second frequency is different than the first frequency.

In one aspect, operating a surgical device includes controlling an ophthalmic surgical device to operate on a portion of an eye. In one aspect, controlling an ophthalmic surgical device includes controlling at least one of a vitrectomy probe, a phacoemulsification probe, and vibrating shears. In one aspect, controlling the light source includes controlling the light source to selectively provide continuous light and the pulses of light. In one aspect, controlling a light source includes: determining if the first frequency is greater than a threshold frequency; and controlling the light source to generate the pulses of light at the second frequency only when the first frequency is greater than the threshold frequency. In one aspect, the threshold frequency is adjustable. In one aspect, operating a surgical device includes providing a first control signal to the surgical device from a computing device communicatively coupled to the surgical device such that the surgical device operates at the first frequency; and controlling a light source includes providing a second control signal to the light source from a computing device communicatively coupled to the light source such that the light source generates the pulses of light at the second frequency. In one aspect, the method further includes receiving, at an interface device communicatively coupled to the computing device, a user input to corresponding to at least one of the first frequency, the second frequency, a threshold frequency, a frequency offset, and a relationship between the first frequency and the second frequency; and generating at least one of the first control signal and the second control signal in response to the user input.

In another exemplary aspect, the present disclosure is directed to an ophthalmic surgical system. The system includes a cutting probe configured to be inserted into an eye, wherein the cutting probe has a periodic movement such that a portion of the eye in contact with the cutting probe acquires the periodic movement; a strobed light source configured to be inserted into the eye and periodically illuminate the portion of the eye; and a computing device communicatively coupled to the cutting probe and the strobed light source, wherein the computing device is configured to provide a first control signal to the cutting probe such that the periodic movement has a first frequency and to provide a second control signal to the strobed light source such that the portion of the eye is illuminated with a second frequency, wherein the second frequency is different than the first frequency.

In one aspect, the computing device is configured to: determine if the first frequency is greater than a threshold frequency; and provide the second control signal only when the first frequency is greater than the threshold frequency. In one aspect, the system further includes an interface device communicatively coupled to the computing device, wherein the interface device is configured to receive a user input corresponding to at least one of the first frequency, the second frequency, a threshold frequency, a frequency offset, and a relationship between the first frequency and the second frequency, such that the computing device generates at least one of the first control signal and the second control signal based on the user input.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the systems, devices, and methods disclosed herein and together with the description, serve to explain the principles of the present disclosure.

These figures will be better understood by reference to the following detailed description.

DETAILED DESCRIPTION

For the purposes of promoting an understanding of the principles of the present disclosure, reference will now be made to the embodiments illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to devices, systems, and methods for improving the visualization of moving tissue during an ophthalmic surgical procedure. A surgical device, such as a cutting probe, operates on the tissue in the eye with a given frequency. When the surgical device is contacted with the tissue, it acquires periodic motion with the same frequency as the surgical device. The moving tissue is illuminated using a strobed light source. The light source generates pulses of light at a frequency higher or lower than the operating frequency of the surgical device. Because the frequencies of the light source and the surgical device are different, any tissue motion that is periodic and synchronous with the surgical device will appear to a surgeon viewing the procedure through a surgical microscope to be slowed down thereby enabling the surgeon to more clearly discern the tissue activity occurring as a result of the surgical procedure.

Figure 1:
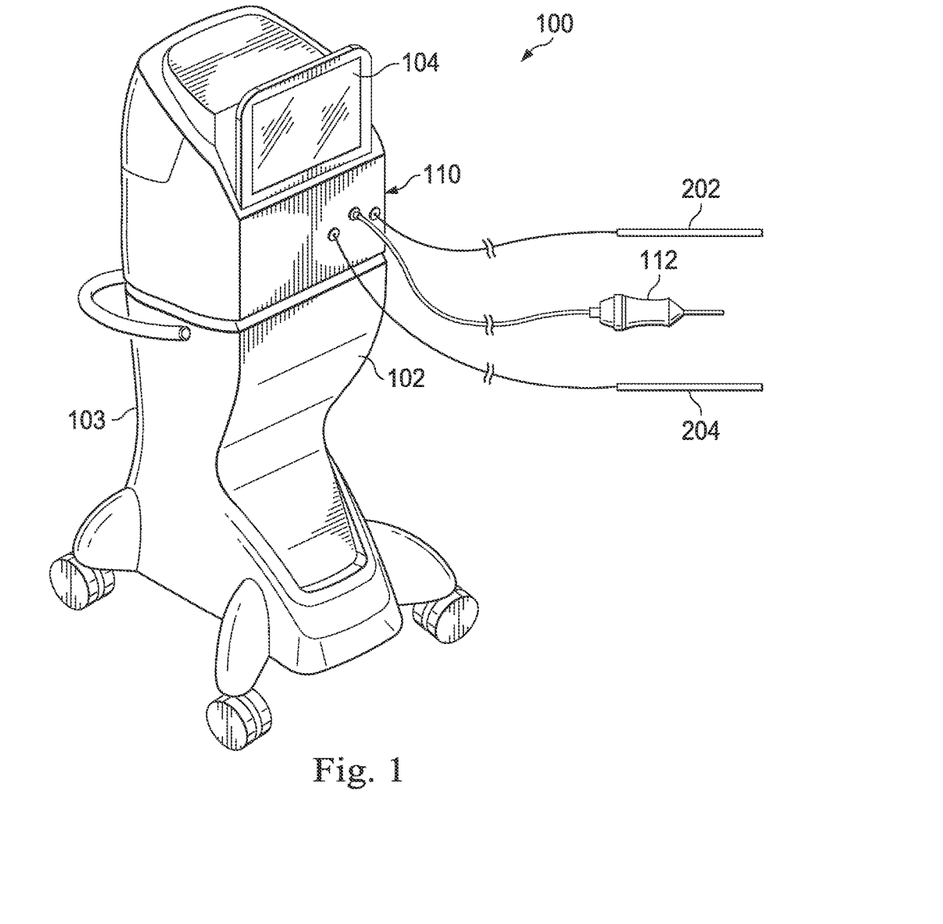
FIG. 1 is an illustration of an ophthalmic surgical system, according to exemplary aspects of the present disclosure.

FIG. 1 illustrates an ophthalmic surgical system 100 according to an exemplary embodiment. The exemplary surgical system 100 includes a console 102 that has a mobile base housing 103 and an associated display screen 104 showing data relating to system operation and performance during an ophthalmic surgical procedure. In various embodiments, the procedure can include a vitrectomy procedure, a cataract procedure, and/or other suitable procedures.

The surgical system 100 includes a probe 112 that is configured to be inserted into the eye. For example, the probe 112 can be a cutting probe, a vitrectomy probe, a phacoemulsification probe, vibrating shears, any instrument including a reciprocating or pulsatile component, and/or other suitable surgical device. An exemplary embodiment of the vitrectomy probe is illustrated in cross-section in FIG. 2. The exemplary vitrectomy probe 112 is a pneumatically driven probe that operates by receiving pneumatic pressure alternating through first and second ports 140 and 142. The probe 112 includes as its basic components a cutter 150 comprising an outer cutting tube 152, an inner cutting tube 154, and a probe actuator or motor shown here as a reciprocating air driven diaphragm 156, all partially encased by a housing 158. The housing 158 includes an end piece 160 at the probe proximal end with the first and second air supply ports 140, 142 and one suction port 162. As can be seen, the cutter 150 extends from the housing 158 and includes a distal end 166. The probe 112 is single-ported in FIG. 2, but it is understood that the probe 112 can be single-ported, double-ported, multi-ported, or alternatingly arranged in other embodiments.

Figure 2:
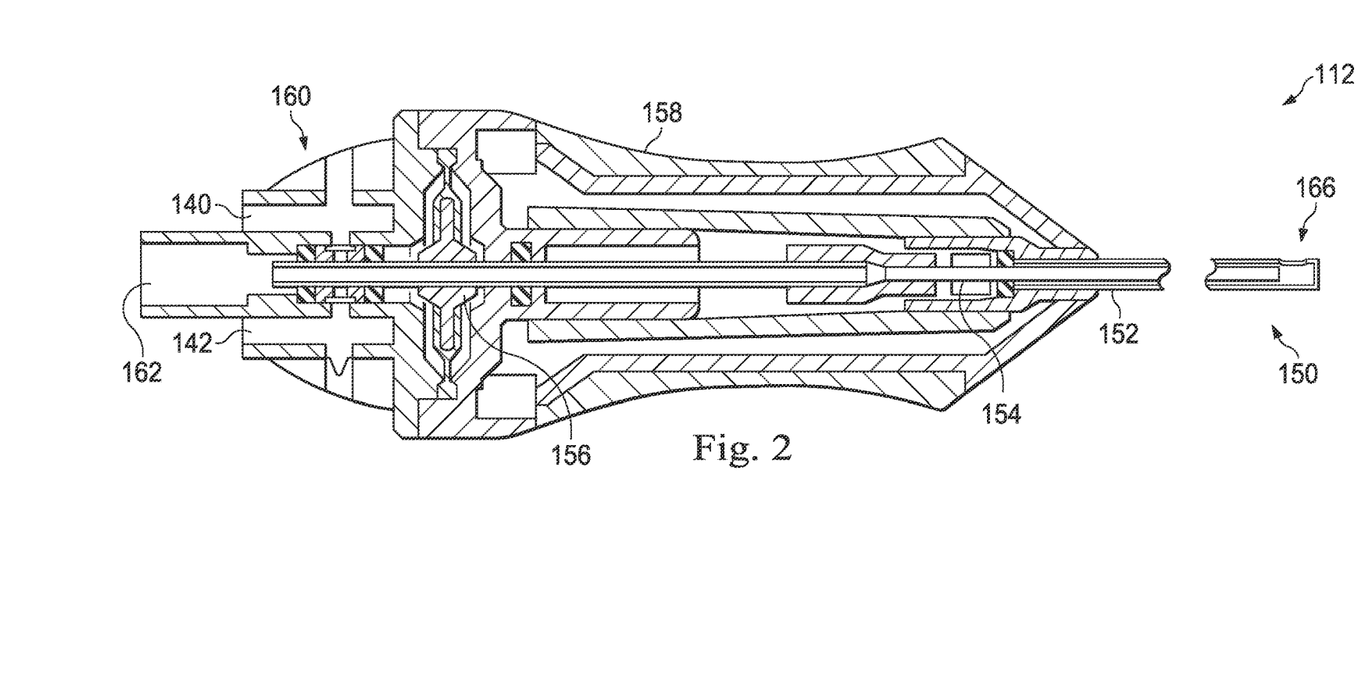
FIG. 2 is a cross-sectional illustration of a vitrectomy probe of the ophthalmic surgical system of FIG. 1, according to exemplary aspects of the present disclosure.

At least an operative portion of the probe 112 (e.g., the cutter 150 of the vitrectomy probe 112) is configured to have pulsatile, oscillatory, and/or otherwise periodic motion that is described by a particular frequency. The surgeon contacts the distal end 166 of the probe 112 to anatomy inside the eye to perform the surgical procedure. The anatomy can acquire a corresponding, synchronous periodic motion when the probe 112 is contacted with the anatomy. The target anatomy can include, by way of non-limiting example, vitreous humor and transparent membranes in a vitrectomy procedure. Other parts of the eye, such as the lens capsule, can be target during a phacoemulsification procedure. In other procedures, portions of the retina and/or other portions of the eye can be in motion.

Referring again to FIG. 1, the surgical system 100 includes one or more light sources 202 and 204. The light sources 202 and 204 have distal portions configured to be inserted into the eye and thus illuminate the tissue inside the eye during the surgical procedure. An exemplary illustration showing the probe 112 and a light source inside of the eye is described in greater detail with respect to FIG. 4. In one embodiment, the light source 202 is a continuous light source, and the light source 204 is a strobed light source. For example, the light source 202 and/or the light source 204 can be an ophthalmic chandelier, spot illuminator, endo-illuminator, fiber optic light source, and/or other suitable surgical illumination device. The light source 202 provides continuous, bright, background, broadband, and/or white light to illuminate the entire surgical field. The light source 202 can include an incandescent light bulb, a halogen light bulb, a metal halide light bulb, a xenon light bulb, a mercury vapor light bulb, a light emitting diode (LED), other suitable components, and/or combinations thereof that provide continuous light.

The light source 204 periodically illuminates the surgical field with pulses of light. For example, the light source 204 can include a flash LED, a pulsed LED, a laser diode, a pulsed laser, a flashtube (e.g., a xenon flashtube, a krypton flashtube, an argon flashtube, a neon flashtube, etc.), other suitable components, and/or combinations thereof that provide pulses of light. The light source 204 also may be any of the same source types as the light source 202 and may be turned on and off to form a strobe effect. The periodic illumination of the light source 204 is described by a particular frequency. As described below, the operator can control the frequency of the light source 204 and/or a computing device can automatically determine and control the frequency of the light source 204.

While FIG. 1 illustrates the probe 112, the light source 202, and the light source 204 as distinct, it is understood that any one or more of these components can be integrated into a single device. For example, the surgical system 100 can include an illuminated probe that integrates the probe 112 and the light source 202. In another example, the light sources 202 and 204 can be integrated such that the integrated light source selectively provides continuous and strobed illumination.

The surgical system 100 includes a control system 110 that is communicatively coupled to the probe 112, light source 202, and/or the light source 204. For example, pneumatic, optical, and/or electrical supply lines extend between the control system 110 and the probe 112, light source 202, and/or the light source 204. In some embodiments, the supply lines may facilitate control and monitoring by also transmitting data between the console 102 and the probe 112, light source 202, and/or the light source 204. In other embodiments, data may be transferred wirelessly between one or more of these components and the console 102. Further, while FIG. 1 illustrates that the light sources 202 and 204 are in direct communication with the console 102, it is understood that one or both can be separate components that are communicatively coupled to the control system 110. In some embodiments, the light is generated by a component spaced from the light source 202 and/or the light source 204. The light can be transmitted to the light source 202 and/or the light source 204 via the supply lines, such as those including optical fibers.

Figure 3:
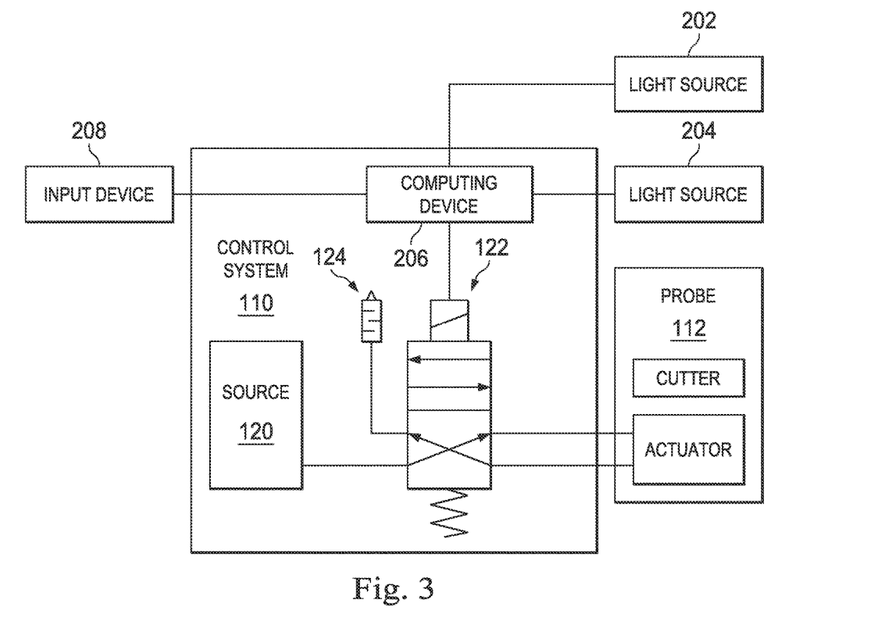
FIG. 3 is a schematic diagram of a control system of the ophthalmic surgical system of FIG. 1, according to exemplary aspects of the present disclosure.

FIG. 3 is a schematic diagram of the control system 110, according to an exemplary embodiment. The control system 110 includes one or more components associated with driving the probe 112, such as a pneumatic pressure source 120, a probe driver shown as an adjustable directional on-off pneumatic driver 122, and a muffler 124. These components can be used to drive a vitrectomy probe, such as the vitrectomy probe 112 of FIG. 2. It is understood that the probe 112 can be driven using any suitable mechanism and/or combination thereof, including pneumatic, electric, piezoelectric, etc. Other suitable components can be implemented in the control system 110 for controlling various types of probes and light sources.

In the embodiment of FIG. 3, the pneumatic driver 122 is a standard four-way valve. As is commonly known, the pneumatic driver 122 has a solenoid that operates to move the driver to one of the two positions depicted. Here, the pneumatic driver 122 is in a position to provide pneumatic pressure to the first port 140 (FIG. 2) of the probe 112, and to vent pneumatic pressure from the second port 142. In this position, pneumatic pressure can pass from the pressure source 120, through the on-off pneumatic driver 122, and to the first port 140 where the pneumatic pressure provides pneumatic power to the vitrectomy probe. At the same time, pneumatic pressure at the second port 142 can pass through the on-off pneumatic driver 122 to the muffler 124 where it is exhausted to the atmosphere. In the other position, the on-off pneumatic driver 122 allows pneumatic pressure to pass from the pressure source 120 to the second port 142 where the pneumatic pressure provides pneumatic power to the vitrectomy probe 112. At the same time, pneumatic pressure at the first port 140 can vent through the on-off pneumatic driver 122 to the muffler 124 where it is exhausted to the atmosphere. The on-off pneumatic driver is configured to receive operating signals from the computing device 206 as further described below. As can be seen, the source 120, the driver 122, the muffler 124, and the probe 112 are in fluid communication with each other along lines representing flow paths or flow lines. The computing device 206 is in electrical communication with the driver 122. Although shown with a single pneumatic driver 122, other embodiments include two pneumatic drivers, one associated with each of the two ports 140, 142. These embodiments operate similar to the manner described, with the drivers being configured to independently receive operating signals from the computing device 206. Yet other arrangements are contemplated.

In operation, pneumatic pressure is directed alternately from the source 120 to the first and second ports 140, 142 to operate the vitrectomy probe 112. The on-off pneumatic driver 122 alternates between its two positions very rapidly to alternatingly provide pneumatic pressure to the first and second ports 140, 142. The pneumatic system thus has a pulsatile, oscillatory, and/or other periodic nature that imparts pulsatile, oscillatory, and/or otherwise periodic motion to the probe 112 and the anatomy to which the probe 112 is contacted. In some embodiments, such as in the case of a vitrectomy probe, the probe 112 itself is relatively stationary. The cutter or the inner cutting tube 154, located inside the needle or the outer cutting tube 152, moves and intermittently interrupts fluid flow. The pulsatile, oscillatory, and/or otherwise periodic tissue motion around the probe 112 can be attributed to pulsatile flow of fluid and vitreous into the port of the needle or the outer cutting tube 152. Thus, it is understood that fluid or tissue proximate to the probe 112 can acquire periodic motion related to movement of at least a portion of the probe 112, even when the probe 112 is not in direct contact with the fluid or tissue.

The control system 110 also includes various components associated with generally directing operation of the surgical system 100. For example, a computing device 206 may include a processing circuit, such as one or more processors in communication with a memory. The processor(s) can execute computer instructions stored on the memory to implement the strobed illumination and surgical procedure control methods described herein. The memory, which is typically a semiconductor memory such as RAM (random access memory), FRAM (ferroelectric RAM), or flash memory, interfaces with the processor(s). As such, the processor(s) can write to and read from the memory, and perform other common functions associated with managing semiconductor memory. In some embodiments, the computing device 206 may include one or more programmable processor units running programmable code instructions. Processing circuit(s) of the computing device 206 can be integrated circuits with power, input, and output pins capable of performing logic functions. In various embodiments, the processor of the computing device 206 is a targeted device controller, or a microprocessor configured to control more than one component of the surgical system 100, and/or a combination thereof.

Generally, the computing device 206 controls various components of the surgical system 100, generates and provides display data to the screen 104, receives and processes input signals and data, generates and outputs command signals, and other functions described herein or necessary to perform the functions described herein. For example, the processor and/or the memory of the computing device 206 can include software containing one or more algorithms defining one or more functions or relationships between input signals and input data (received from an interface device 208 (described below), the probe 112, the light source 202, and/or the light source 204). For example, the algorithms may dictate activation or deactivation command protocols/signals (e.g., by initiating, signaling, and/or triggering the cutting mechanism of the probe 112, the pulsing/flashing mechanism of the light source 204, etc.) depending on the received input data or mathematical derivatives thereof. For example, in some embodiments, the computing device 206 controls operating frequencies of the cutting mechanism of the probe 112 (e.g., the cutter 150 shown in FIG. 2) and/or pulsing/flashing of the light source 204. In some embodiments, the computing device 206 performs logic functions based on inputs from the interface device 208, the probe 112, the light source 202, and/or the light source 204, such as comparing and determining if the desired actuation or cutting frequency for the probe 112 is different than the desired pulsing/flashing frequency for the light source 204. The computing device 206 can provide a control signal to one or both of the probe 112 and the light source 204 to change the operating frequency. In some embodiments, the computing device 206 controls the supply of power from a power source to the probe 112, the light source 202, and/or the light source 204.

The computing device 206 is communicatively coupled to the interface device 208 which allows a user to input data, operating parameters, input signals, etc. The interface device 208 may comprise any of a variety of ON/OFF switches, buttons, toggles, wheels, digital controls, touchscreen controls, or other user interface components. In some embodiments, the interface device 208 is integrally disposed on the console 102. In some embodiments, the interface device 208 is a distinct component, such as, by way of non-limiting example, a surgical footswitch, a remote control device, a touchscreen control device, and/or another computing device. The interface device 208 facilitates control, monitoring, data processing, etc., for the probe 112, the light source 202, and/or the light source 204. In response to a user input, the interface device 208 can generate and transmit an input signal to the computing device 206. For example, the operator can use the interface device 208 to provide a user input to activate the probe 112, the light source 202, and/or the light source 204. The operator can also provide a user input to set a desired cutting frequency for the probe 112 and a pulsing/flashing frequency for the light source 204. The computing device 206 receives and processes the input signal. The computing device 206 generates control signals in response to the user input. The computing device 206 also transmits the control signals to the probe 112, the light source 202, and/or the light source 204. Generally, the interface device 208 is configured to receive an input signal representative of an actuation or operating frequency of the probe 112, an illumination or pulsing/flashing frequency of the light source 204, a threshold frequency (described below) associated with strobed illumination is provided, a frequency offset between the operating frequencies of the probe 112 and the light source 204, and/or a relationship between the operating frequencies of the probe 112 and the light source 204.

The probe 112, the light source 202, the light source 204, and the interface device 208 are operatively/communicatively coupled to the console 102 (and, in particular, the computing device 206) by way of wired or wireless communication mechanisms. In that regard, the control system 110 can include a data transmission module and/or a network communication interface to facilitate communication between various components of the surgical system 100. In some embodiments, the processor of computing device 206 can send controls signals to and/or receive input signals from the probe 112, the light source 202, the light source 204, and/or the interface device 208, and/or various accessory devices via the wireless or wired mechanisms. The computing device 206 can use the received data to control, direct, or adjust the operation of the probe 112, the light source 202, and/or the light source 204. For example, the probe 112 can transmit its operating frequency to the computing device 206. The computing device 206 can determine that the operating frequency is above a threshold frequency before sending an activation signal to the light source 204 to begin pulsing/flashing. Contemplated wireless communication methods include, by way of nonlimiting example, cooperating transmitters and receivers positioned on various components of the surgical system 100.

Figure 4:
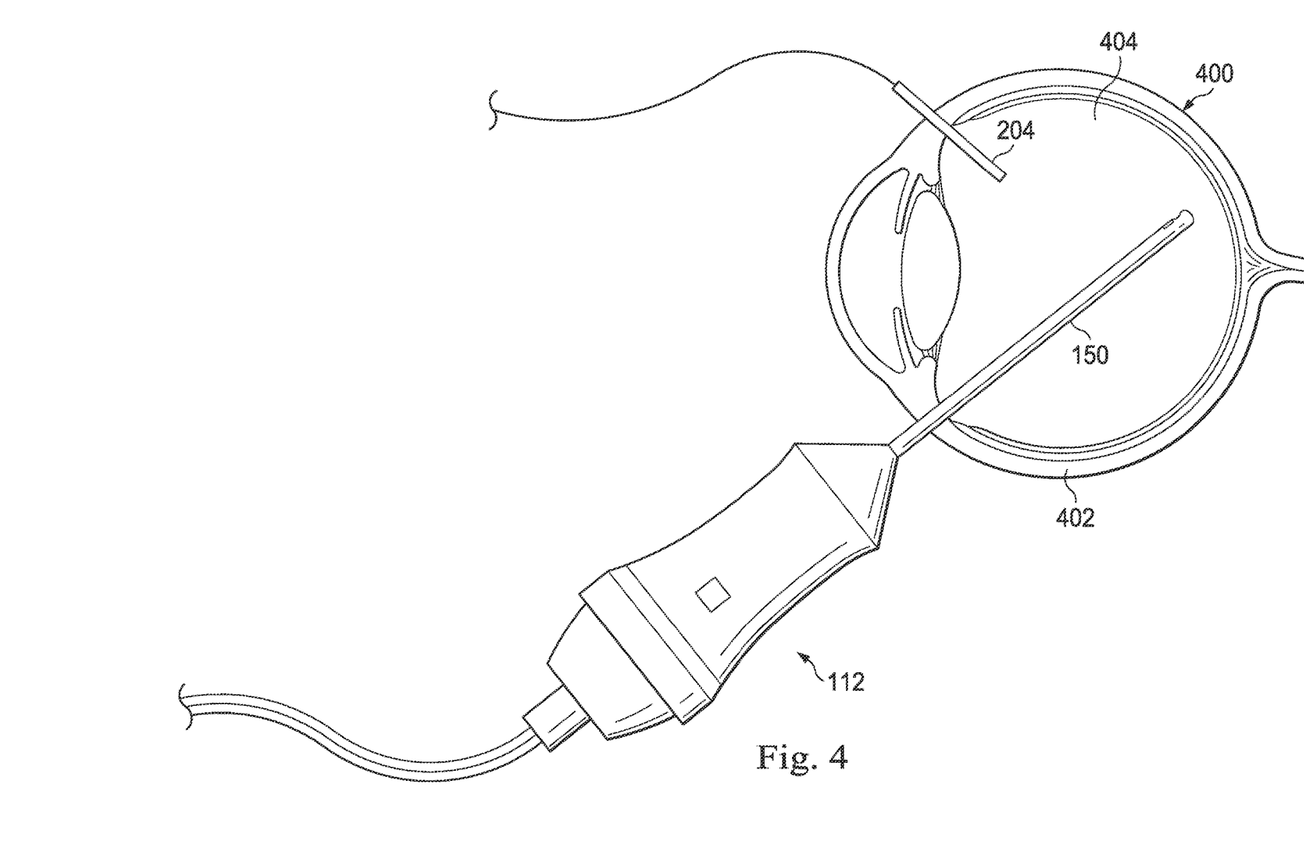
FIG. 4 is a partial cross-sectional illustration of a surgical device and a light source in situ in an eye, according to exemplary aspects of the present disclosure.

FIG. 4 illustrates a partial cross-sectional view of an eye 400 undergoing a procedure involving the surgical system 100 and the light source 204. The procedure can be a vitrectomy procedure in some embodiments, during which a surgeon typically inserts the cutter 150 of the vitrectomy probe 112 into the posterior segment of the eye (e.g., the vitreous chamber 404) via an incision through the sclera 402 in the pars plana. Such an incision is called a sclerotomy. The surgeon also inserts one or more light sources (e.g., the light source 202 and/or the light source 204) and an infusion cannula (not shown) into the eye via similar incisions, and may sometimes substitute an aspiration probe for the vitrectomy probe 112. While viewing the posterior segment under a microscope and with the aid of the light source 204, the surgeon cuts and aspirates away vitreous or other tissue using the vitrectomy probe 110 to gain access to the area of interest (e.g., the site of a retinal detachment or tear). The vitrectomy probe 112 has an actuation or cutting frequency that is transferred to the vitreous and/or other tissue when the cutter 250 is in contact with it. In some embodiments, the light source 204 selectively transmits continuous light until the surgeon determines that periodic illumination is needed.

Then, the computing device 206 can control the light source 204 to selectively, periodically illuminate the surgical field at a frequency that is different than a cutting frequency to facilitate the surgeon's view of the moving tissue. That is, as a result of the strobed illumination, the tissue being cut or any attached tissue appears to slow down and move at a frequency equal to the difference between the cutting frequency and the pulsing/flashing frequency.

The surgeon can also use the vitrectomy probe 110 to remove any membrane that has contributed to the retinal detachment or tear. During this portion of the surgery, a saline solution is typically infused into the eye via the infusion cannula to maintain the appropriate intraocular pressure. The infusion line is a specialized type of probe used to deliver replacement fluid or irrigation fluid into the vitreous chamber 404 during vitrectomy procedures. A pressure level of the irrigation fluid may be increased or decreased by the control system 110. The vitrectomy probe 110, one or more light sources, and/or the infusion line may be coupled to a console, such as the console 102 shown in FIG. 1.

Figure 5A:
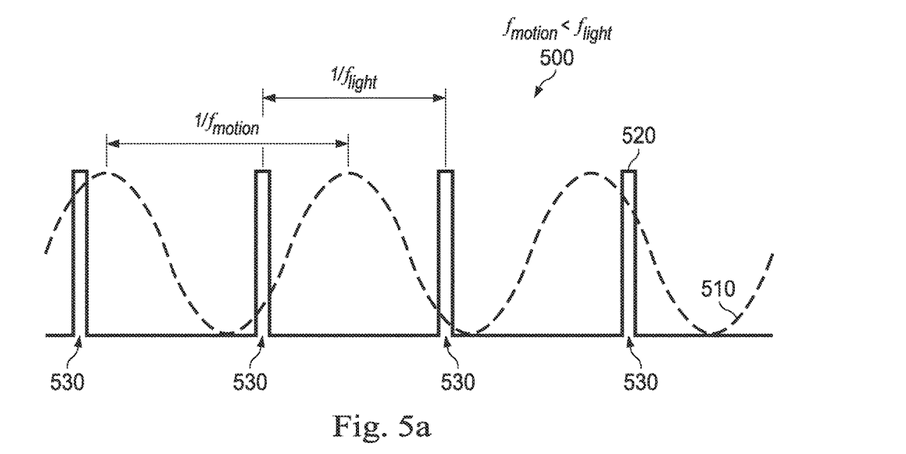
FIGS. 5a and 5b are graphs illustrating operating frequencies of a surgical device and a light source, according to exemplary aspects of the present disclosure.
Figure 5B:
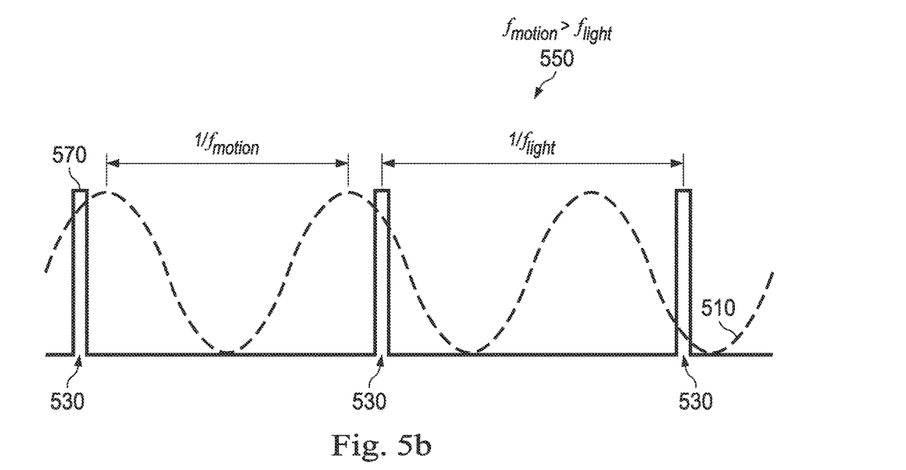

FIGS. 5a and 5b are graphs 500 and 550 respectively illustrating operating frequencies of the probe 112 and the light source 204, according to exemplary embodiments. The waveform 510 is representative of the periodic motion of the probe 112 and the synchronous, periodic motion of the tissue in contact with the probe 112. The motion can be described by a frequency $f_{motion}$. In various embodiments, the frequency of the motion $f_{motion}$ can be between about 3 Hz (200 cuts per minute or cpm) and about 133 Hz (8000 cpm), between about 8 Hz (500 cpm) and about 133 Hz (8000 cpm), between about 75 Hz (4500 cpm) and about 133 Hz (8000 cpm), and other suitable values. For example, while the maximum frequency of extant vitrectomy probes is about 133 Hz (8000 cpm), the principles described herein can be implemented for frequencies greater than 133 Hz (8000 cpm) up to and exceeding 250 Hz (15000 cpm).

The waveforms 520 and 570 are representative of the pulsing/flashing of the light source 204. When the waveforms 520 and 570 are high, the light source 204 is shining and illuminating the surgical field. When the waveforms 520 and 570 are low, the light source 204 is not shining. The periodic illumination can be described by a frequency $f_{light}$. The range of values of the frequency $f_{light}$ can be similar to the frequency of the motion $f_{motion}$. However, as described herein, the frequency $f_{light}$ can be offset from the frequency $f_{motion}$.

In some embodiments, the light source 204 is controlled (e.g., by the computing device 206) to provide periodic illumination only when the frequency of motion $f_{motion}$ greater than a threshold frequency. The threshold frequency can be between about 25 Hz and about 80 Hz, between about 25 Hz and about 75 Hz, between about 60 Hz and about 75 Hz, including values such as 25 Hz, 35 Hz, 50 Hz, 60 Hz, 75 Hz, and/or other suitable values. In some embodiments, a minimum frequency of illumination $f_{light}$ can be approximately equal to the threshold frequency. A maximum frequency $f_{light}$ can be approximately equal to the sum of the frequency of motion $f_{motion}$ and an offset (described below) between the frequency $f_{light}$ and the frequency $f_{motion}$. For example, when the threshold frequency is 75 Hz (4500 cpm), the frequency $f_{light}$ can be any value greater than about 75 Hz, up to and exceeding 250 Hz. In some embodiments, the frequency $f_{light}$ can be between about 75 Hz and 250 Hz, between about 75 Hz and about 150 Hz, between about 75 Hz and about 133 Hz, and/or other suitable values. The surgeon and/or the computing device 206 can change the frequency $f_{light}$ as needed during the surgical procedure, such as in response to frequency of the motion $f_{motion}$ or based on user preferences. In some embodiments, the threshold frequency corresponds to the critical flicker fusion (CFF) rate. The CFF rate is a quantity in psychophysics describing the frequency beyond which flicker or individual images in a successive image set are no longer independently perceivable by an observer.

According to embodiments of the present disclosure, the probe 112 and the light source 204 can be operated with frequencies that are different. That is, the light source 204 provides periodic illumination with the frequency $f_{light}$ higher or lower than the frequency $f_{motion}$ of the probe 112. In such circumstances, the surgeon viewing the procedure through a surgical microscope sees the illuminated tissue moving at frequency equal to the absolute value of the difference between the frequency $f_{light}$ and the frequency $f_{motion}$. For example, if the probe 112 is being operated with a cut rate of 7500 cpm (125 Hz), the light source 204 can be controlled to illuminate the surgical field with a frequency of 115 Hz or 135 Hz. This would cause any synchronous, periodic tissue motion to appear to have a frequency of 10 Hz (absolute value of 125 Hz-115 Hz and 125 Hz-135 Hz). As described below, the sign/polarity of the difference determines whether the tissue motion appears forward or in reverse. Because the tissue appears to move at a slower 10 Hz (compared to the original 125 Hz), an operator can more clearly see the amplitude and shape of the tissue motion, and carry out the surgical procedure accordingly. The apparent slower motion also allows for the operator to confirm that the probe is functioning as intended. Without periodic illumination, for example, the moving component of the probe is typically moving too quickly for the operator to visualize.

The periodic illumination algorithm described herein takes advantage of the related principles of sampling and aliasing. Generally, a signal can be sampled, and the samples can be used to reconstruct the original signal. A periodic signal can be sampled at a given sample rate/frequency (samples per second). Correspondingly, a periodic signal can be described by the number of cycles per sample. In a typical signal processing context, the sampling frequency is selected to be high enough that the true signal is not obscured when the samples are used to reconstruct the signal. That is, the sampling frequency should be high enough that the reconstructed signal is the true signal and not one of the signal's aliases. This condition is generally satisfied when half of the sampling rate (known as the Nyquist frequency) is greater than the frequency of the true signal. In the context of the present disclosure, the signal is the motion of the probe 112 and/or the corresponding, synchronous motion of the tissue. The sampling rate is the pulsing/flashing frequency of the light source 204. Unlike the typical signal processing context, embodiments of the present disclosure actually seek to create an alias of the true signal. In particular, the periodic illumination algorithm described herein seeks to create an alias of the true signal with a frequency that is slow enough to be perceptible by the surgeon. Thus, the frequency of the periodic illumination (the sampling frequency) can be selected such that sampled aliased motion is closer to zero hertz and therefore able to be perceived by the surgeon. For ratios of signal frequency to sampling frequency that are near unity, the resulting apparent frequency of the signal will be the difference between the signal frequency and the sampling frequency.

If the probe 112 and the light source 204 are operated at the same frequency, the periodically moving tissue would appear to be stationary, which is not helpful for the operator to carefully evaluate the surgical field. The strobed illumination described herein is unlikely to have deleterious effects on viewing the surgical field because, with a sufficiently high frequency of illumination by the light source 204, any stationary tissue or non-periodically moving tissue would appear as it would ordinarily appear with continuous light.

FIGS. 5a and 5b illustrate that the surgeon sees the motion of the tissue during intervals 530 when the tissue is periodically illuminated. Because the frequencies of the motion and the light are different, the surgeon sees different portions of the periodic tissue motion, represented by the waveform 510, during successive intervals 530. Graph 500 shows the waveforms 510 and 520 when the frequency of the motion $f_{motion}$ is less than the frequency of the light $f_{light}$. That is, the period ($1/f_{motion}$) associated with the motion is greater than the period ($1/f_{light}$) associated with the light. The periodic motion of the tissue would appear to the surgeon to be occurring in reverse. This is represented by earlier portions of the waveform 510 being illuminated during successive intervals 530. Graph 500 shows the waveforms 510 and 570 when the frequency of the motion $f_{motion}$ is greater than the frequency of the light $f_{light}$. That is, the period ($1/f_{motion}$) associated with the motion is less than the period ($1/f_{light}$) associated with the light. The periodic motion of the tissue would appear to the surgeon to be occurring in a forward manner. This is represented by later portions of the waveform 570 being illuminated during successive intervals 530.

Regardless of whether the tissue motion is forward or in reverse, the tissue motion appears slowed down when the frequencies $f_{motion}$ and $f_{light}$ are different. The physiological difference between reverse and forward motion of the tissue may or may not be distinguishable to the surgeon. In some embodiments, the surgeon may have a preference to view the tissue motion in a forward manner or in reverse. For example, when the frequency $f_{light}$ is greater, the surgical field may be more illuminated. When the frequency $f_{motion}$ is greater, the tissue motion appears in a forward manner. The surgeon can control the cutting frequency of the probe 112 and the pulsing/flashing frequency of the light source 204 using the interface device 208 (FIG. 3) such that the cutting frequency is greater than or less than the pulsing/flashing frequency. That is, the surgeon can control the magnitude and the sign/polarity of the frequency difference. The interface device 208 generates and provides a signal to the computing device 206 in response to the user input. The computing device 206 (FIG. 3) can process the input signal and transmit a control signal to the probe 112 and/or the light source 204 to operate at particular frequencies.

The waveforms in graphs 500 and 550 are illustrative of the periodic nature of the motion of the probe 112, the motion of the tissue, and the illumination provided by the light source 204. The sinusoidal and/or square wave shapes of the waveforms 510, 520, and 570 are not intended to be limiting.

Figure 6:
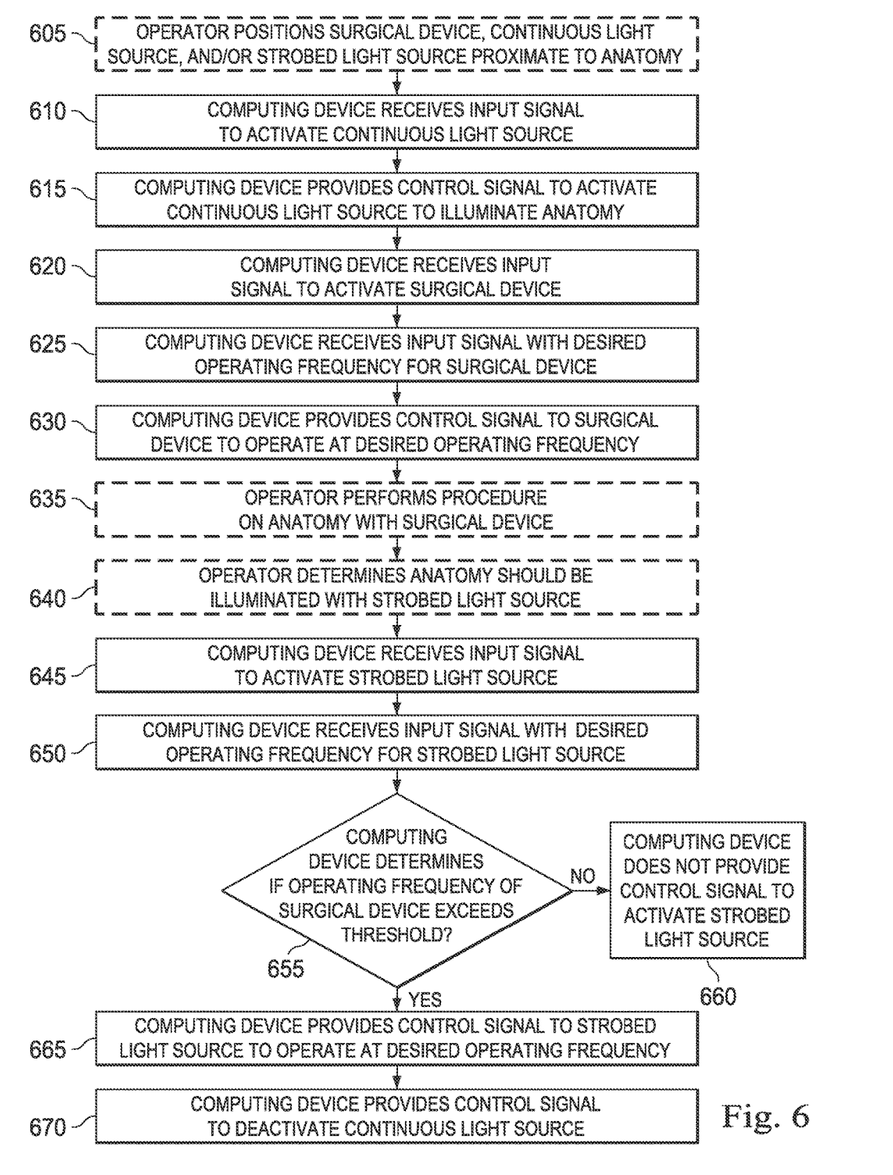
FIG. 6 is a flowchart illustrating a method of treating an ophthalmic condition, according to exemplary aspects of the present disclosure.

FIG. 6 is a flowchart of an exemplary method of operating the surgical system 100 in treating an ophthalmic condition according to one embodiment of the present disclosure. As illustrated, the method includes a number of enumerated elements, but embodiments of the method may include additional elements before, after, and in between the enumerated elements. In some embodiments, one or more of the enumerated elements may be omitted or performed in a different order.

The illustrated embodiment begins at 605 in which an operator positions a surgical device (e.g., the probe 112), a continuous light source (e.g., the light source 202), and/or strobed light source (e.g., the light source 204) proximate to anatomy. For example, during a vitrectomy procedure, the surgeon can insert the probe 112, the light source 202, and/or the light source 204 through a sclera into a vitreous chamber of a patient. At 610, the method includes the computing device (e.g., the computing device 206) receiving an input signal to activate the continuous light source. For example, the surgeon can provide a user input at the interface device 208 to activate the light source 202 to provide background illumination for the surgical field. At 615, the method includes the computing device generating and/or transmitting the control signal to activate the continuous light source to illuminate the anatomy. In some embodiments, the continuous light and strobed light are provided by the same light source (e.g., the light source 204). For example, the light source 204 can provide continuous light until the cutting frequency of the probe 112 exceeds a threshold value and/or the surgeon determines that the light source 204 should periodically illuminate the surgical field, at which point in time, the light source may then be controlled to strobe in a desired manner.

At 620, the method includes the computing device receiving an input signal to activate the surgical device. For example, the surgeon can provide a user input at the interface device 208 to activate the probe 112 so that the surgeon can begin cutting tissue. At 625, the method includes the computing device receiving an input signal with the desired operating frequency for the surgical device. For example, the surgeon can provide a user input at the interface device 208 to specify the desired cut rate for the probe 112. In some embodiments, the surgeon can modify the cut rate one or more times during the surgical procedure. At 630, the method includes the computing device generating and/or transmitting a control signal to the surgical device to activate and/or operate at the desired operating frequency. For example, the computing device 206 can provide a control signal to the driver 122 and/or the probe 112 to operate with the desired cut rate.

At 635, the method includes the operator performing the surgical procedure on the anatomy with the surgical device. For example, the surgeon can use the probe 112 to cut and aspirate vitreous from the eye. At 640, the method includes the operator determining that the anatomy should be illuminated with the strobed light source. For example, at some point during the surgical procedure, the cutting frequency of the probe 112 can become high enough that the surgeon needs illumination from the strobed light source to slow down the periodic tissue motion. In some embodiments, the computing device 206 can provide an audio/visual/tactile alert to the surgeon when the cutting frequency of the probe 112 exceeds the threshold value. The surgeon would then know that light source 204 can periodically illuminate the anatomy.

At 645, the method includes the computing device receiving an input signal to activate the strobed light source. For example, the surgeon can provide a user input at the interface device 208 to activate the light source 204 to provide periodic illumination. Alternatively, the control system 110 may automatically activate the light source 204 based on received information or data. At 650, the method includes the computing device receiving an input signal with the desired operating frequency for the strobed light source. For example, the surgeon can provide a user input at the interface device 208 to specify the desired pulsing/flashing rate for the light source 204. In other embodiments, the system automatically selects the desired pulsing/flashing rate. In some embodiments, the surgeon can modify the pulsing/ flashing rate one or more times during the surgical procedure. For example, the surgeon can modify the pulsing/flashing rate whenever the cut rate of the probe 112 is modified.

In some embodiments, the desired operating frequencies of the light source 204 and the probe 112 are completely configurable by the surgeon. Thus, the differential between the operating frequencies of the light source 204 and the probe 112 is also completely configurable by the surgeon. In some embodiments, the computing device 206 controls the operating frequencies of the light source 204 and the probe 112 to have a fixed or constant frequency offset. For example, the surgeon may prefer for moving tissue to appear to have a frequency of 10 Hz when the surgical field is illuminated with periodic light. Thus, the computing device 206 can automatically determine the operating frequency of the light source 204 based on the cutting frequency of the probe 112. For example, the operating frequency of the light source 204 can be plus or minus 10 Hz relative to the operating frequency of the probe 112. In some embodiments, the computing device 206 changes the illumination frequency of the light source 204 as the cutting frequency of the probe 112 changes. The frequency offset or differential can be changed based on the cutting frequency of the probe 112. Generally, the illumination frequency and/or frequency offset can be mathematically related to the actuation frequency of the probe 112. The illumination frequency and/or frequency offset can be a function of the actuation frequency of the probe 112. For example, the computing device 206 can increase the frequency offset as the cutting frequency increases, and vice versa. That is, the computing device 206 can control the illumination frequency to increase at a faster rate than the rate that the cutting frequency increases (and vice versa). Thus, the difference between the illumination frequency and the cutting frequency increases as the cutting frequency increases (and vice versa). In this manner, the operator is provided with a perception of higher motion frequency with higher actuation frequency (and vice versa).

In various embodiments, the operating frequencies of the light source 204 and the probe 112 can be selected (e.g., by the surgeon or the computing device 206) such that resulting apparent motion is slow enough for a surgeon to appreciate but not so slow that it takes too long for the tissue motion to complete one cycle. That is, the surgeon should see the entire motion occurring quickly enough to react appropriately. For example, the differential can be selected such that apparent frequency of the tissue is as fast as possible without being blurry. This would provide good perception of the moving tissue for the surgeon, while allowing the tissue to complete a full cycle in a relatively short time so that the surgeon can quickly and appropriately respond. In various embodiments, the frequency offset or differential between the operating frequencies is between about 2 Hz and about 20 Hz, about 5 Hz and about 12 Hz, between about 8 Hz and about 12 Hz, between about 10 Hz and 12 Hz, including values such as 2 Hz, 5 Hz, 8 Hz, 10 Hz, 12 Hz, 15 Hz, 18 Hz, 20 Hz, and other suitable values.

At 655, the method includes the computing device determining if the operating frequency of the surgical device exceeds a threshold frequency. For example, the computing device 206 can determine if the cutting frequency of the probe 112 is above the CFF rate or a user-specified threshold frequency. When the operating frequency of the surgical device does not exceed the threshold frequency, at 660, the computing device does not provide the control signal to activate the strobed light source. With 655 and 660, the computing device 206 ensures that light source 204 does not provide periodic illumination with perceptible flickering, which could be distracting to the surgeon during the procedure. Constant illumination for the surgical field can continue to be provided, such as by the light source 204 or another light source, when the operating frequency of the surgical device does not exceed the threshold frequency.

At 665, the method includes the computing device providing a control signal to the strobed light source to operate at the desired operating frequency. For example, the computing device 206 can transmit a control signal to the light source 204 such that it periodically illuminates moving anatomy within the eye. In some embodiments, the computing device 206 can compare the operating frequency of the surgical device to the desired operating frequency of the strobed light source to determine that the frequencies are different. If the frequencies are not different, the computing device 206 can automatically adjust the operating frequency of the probe 112 and/or the light source 204 so that they are different. For example, the computing device 206 can control the illumination frequency to have a constant frequency offset relative to the operating or actuation frequency of the probe 112. As another example, the computing device 206 can control the illumination frequency based on an algorithm (e.g., the illumination frequency is a function of the operating or actuation frequency of the probe 112). In some embodiments, computing device 206 can provide an audio/visual/tactile alert to the surgeon to indicate that the operating frequencies are the same and need to be adjusted. In some embodiments, the display device 104, the interface device 208, and/or a dial, display, or other suitable component of console 102 can display the set and/or actual operating frequencies of the probe 112 and the light source 204 so that surgeon is unlikely to input a desired pulsing/flashing frequency that is the same as the cutting frequency.

At 670, the method includes the computing device providing a control signal to deactivate the continuous light source. For example, in some embodiments, when the strobed light source is periodically illuminating the surgical field, the continuous light source is deactivated. Thus, the pulsing/flashing of the light source 204 and the apparent, slowed motion of the tissue is more pronounced. In other embodiments, the constant light source remains activated and provides background illumination while the strobed light source provides periodic illumination.

The systems and methods disclosed herein may be used to enable the improved visualization of probe-induced motion of mobile tissue during surgical procedures with high cut rates. With continuous illumination and high cut rates, any periodic motion may appear blurred, possibly preventing the surgeon from seeing the extent of the motion. By choosing an appropriate frequency differential for the strobed illumination, the tissue motion may not be blurred and may appear to be occurring at a frequency high enough to be noticed. This allows the surgeon to carefully evaluate the tissue before cutting.

Persons of ordinary skill in the art will appreciate that the embodiments encompassed by the present disclosure are not limited to the particular exemplary embodiments described above. In that regard, although illustrative embodiments have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A method of treating an ophthalmic condition, the method comprising:
   operating a surgical device at a first frequency such that anatomy moves at the first frequency when the surgical device is contacted therewith;
   receiving a threshold frequency from a user;
   controlling a light source to provide pulses of light at a second frequency to illuminate the moving anatomy, wherein the second frequency is different than the first frequency;
   wherein controlling the light source includes a computing device:
   determining if the first frequency is greater than the received threshold frequency; and
   controlling the light source to generate the pulses of light at the second frequency only when the first frequency is greater than the threshold frequency.

2. The method of claim 1, wherein the threshold frequency is adjustable.

3. The method of claim 1, wherein operating the surgical device includes controlling an ophthalmic surgical device to operate on a portion of an eye.

4. The method of claim 3, wherein controlling the ophthalmic surgical device includes controlling at least one of a vitrectomy probe, a phacoemulsification probe, and vibrating shears.

5. The method of claim 1, wherein controlling the light source includes controlling the light source to selectively provide continuous light and the pulses of light.

6. The method of claim 1, further comprising:
   receiving a frequency offset between the first frequency and the second frequency for operating the light source; and
   determining the second frequency by adding the frequency offset to the first frequency.

7. The method of claim 6, wherein the frequency offset is received from a user through an interface device.

8. The method of claim 1, wherein controlling the light source comprises controlling a flash LED (light emitting diode), a pulsed LED, a laser diode, a pulsed laser, or a flashtube.

9. The method of claim 1, wherein the threshold frequency corresponds to a critical flicker fusion (CFF) rate.

10. The method of claim 1, wherein controlling the light source comprises providing constant illumination when the first frequency is less than the threshold frequency.

* * * * *